United States Patent [19]
Trost

[11] Patent Number: 6,066,245
[45] Date of Patent: May 23, 2000

[54] METHOD AND APPARATUS FOR SCANNING FLUORESCENTLY LABELED PARTICLES

[75] Inventor: Peter Trost, Carlsbad, Calif.

[73] Assignee: Genetic Biosystems, Inc., San Diego, Calif.

[21] Appl. No.: 08/774,023

[22] Filed: Dec. 27, 1996

[51] Int. Cl.[7] .......................... G01N 27/26; G01N 27/447
[52] U.S. Cl. ......................... 204/461; 204/612; 356/317; 356/344; 385/33; 422/82.08
[58] Field of Search ..................................... 204/452, 456, 204/461, 466, 467, 606, 603, 616, 618; 356/344, 417, 317; 385/33; 422/82.08; 436/94, 172

[56] References Cited

U.S. PATENT DOCUMENTS

| | | | |
|---|---|---|---|
| 4,573,761 | 3/1986 | McLachlan et al. | 350/96.24 |
| 4,650,336 | 3/1987 | Moll | 356/417 |
| 4,707,134 | 11/1987 | McLachlan et al. | 356/342 |
| 4,753,530 | 6/1988 | Knight et al. | 356/73 |
| 5,030,000 | 7/1991 | Kanda | 356/40 |
| 5,091,652 | 2/1992 | Mathies et al. | 250/458.1 |
| 5,112,127 | 5/1992 | Carrabba et al. | 356/301 |
| 5,202,558 | 4/1993 | Barker | 250/227.21 |
| 5,274,240 | 12/1993 | Mathies et al. | 250/458.1 |
| 5,402,508 | 3/1995 | O'Rourke et al. | 385/31 |
| 5,421,339 | 6/1995 | Ramamujan et al. | 128/665 |
| 5,485,536 | 1/1996 | Islam | 385/31 |
| 5,538,613 | 7/1996 | Brumley et al. | 204/612 |
| 5,543,018 | 8/1996 | Stevens et al. | 204/461 |
| 5,606,170 | 2/1997 | Saaski et al. | 250/458.1 |
| 5,625,459 | 4/1997 | Driver | 385/33 |
| 5,652,810 | 7/1997 | Tipton et al. | 385/12 |

Primary Examiner—Robert J. Warden, Sr,
Assistant Examiner—Kaj K. Olsen
Attorney, Agent, or Firm—Lyon & Lyon LLP

[57] ABSTRACT

A system and method for illuminating an optically active sample and collecting scattered light emitted by the sample. Preferably, the sample is a fluorescently labeled and fluoresces light. The system includes a fiber optic bundle, including at least one illuminating fiber for emitting an illuminating beam, and including at least one collecting fiber disposed adjacent the illuminating fiber. The system further includes an optical apparatus for focusing the illuminating beam, for directing the focused illuminating beam to the fluorescently labeled sample to cause the sample to emit fluoresced light, and for directing at least some of the fluoresced light emitted by the sample to the collecting fiber.

23 Claims, 3 Drawing Sheets

METHOD AND APPARATUS FOR SCANNING FLUORESCENTLY LABELED PARTICLES

BACKGROUND OF THE INVENTION

1. Field of the Invention

This invention relates to a method and system for illuminating a sample and collecting scattered light from the sample. More particularly, the present invention relates to a method and system for illuminating an optically active sample and collecting scattered light from the sample in which a fiber optic bundle and a lens set is used for laser illumination and fluorescence collection.

2. Description of Related Art

Various techniques exist for separating particles, such as proteins, nucleic acids, and the like. For example, polyacrylamide gel electrophoresis separation can be used to separate two polypeptides of the same size but of different isoforms, or to separate polypeptides having very small differences in size. In addition, polyacrylamide gel electrophoresis can be used for DNA sequencing, in which nucleic acids are separated based on the size of DNA fragments.

In DNA sequencing, a thin gel is sandwiched between two plates (e.g., glass plates) having discrete lanes arrayed from one end of the glass plates to another. DNA fragments are introduced into the discrete lanes at one end of the plates. An electric field is then applied along the gel from either end of the plates, causing the DNA fragments to propagate through the gel from one end of the plates to the opposite end. The DNA fragments propagate in bands (or clumps), each having a discrete length measured by a number of nucleotides. Thus, for example, a band may be 10,000 nucleotides in length. The velocity of each band through the gel is dependent on the size (mass) of the DNA fragment and the charge on the fragment, with each band propagating at a different velocity. Consequently, each band in a lane passes a predetermined point along the lane at a discrete time.

The bands of DNA fragments may be detected using a variety of methods and associated apparatus. For example, as disclosed in U.S. Pat. No. 5,543,018, uncharged bands of DNA fragments can be detected by directing an incident beam of polarized light toward a predefined detection zone. The incident beam passes through the detection zone, resulting in an exiting beam, which is then analyzed to determine if its polarization differs from that of the incident beam. Differences in polarization between the incident beam and exiting beam are used to detect bands of DNA fragments.

In another detection technique, fluorescently labeled DNA fragments are illuminated by a narrow-band light source, focused into a small spot on the gel, at the wavelength that excites the fluorescent label. The labels within the illuminating spot, in turn, fluoresce light in an omnidirectional fashion that is shifted in wavelength from the illuminating spot. The fluoresced light is then collected and focused onto a light detector. The spot is repeatedly scanned across the gel in a direction perpendicular to the electric field. This scanning builds an image of the bands in the gel, because the bands are propagating along the direction of the electric field. The maximum resolution of the resultant image is determined by the size of the illuminating spot, for example, 50 $\mu$m.

Currently, a confocal system is used for scanning the spot across the gel. FIG. 1 shows a typical confocal system 100, in which the same lens 102 is used to focus an illuminating spot 104 into a gel 106 and to collect fluoresced light emitted by a sample (not shown) within the gel 106. The illuminating beam 110 is produced by a laser diode 112 and is then collimated by an aspherical lens 114. An interference filter 116 is used to reject laser light from the beam 110 that is within the spectrum of the fluoresced light. The filtered beam 110 then propagates to a dichroic mirror 118 that reflects the beam 110 at a 90 degree angle. The reflected beam 110 is directed to a moving mirror and lens set 102, which moves along the beam 110, thus scanning the focused spot 104 across the gel 106, which is supported between two glass plates 108. The lens 102 is diffraction limited and has a large numerical aperture so that a significant fraction of fluoresced light emitted by the sample is collected and formed into a well collimated beam 108 of fluoresced light. The fluoresced light beam 108 propagates back along the path of the illuminating beam 110 to the dichroic mirror 118. The mirror 118 is selected so that the fluoresced light beam 108 is transmitted through the mirror 118, propagating through a filter 122 that rejects all light outside the spectra of the fluoresced light 112. A lens 124 then focuses the fluoresced light beam 120 onto an avalanche photodiode detector and amplifier 126.

Although confocal system 100 is efficient and relatively simple, its suffers a significant drawback in that it is difficult to align. Alignment of the parts comprising system 100 is completely interdependent, because an adjustment to any part of the system 100 requires that all other parts of the system be adjusted as well. This causes significant problems in mass manufacturing applications. Moreover, confocal systems require a stable mechanical system to maintain the system in alignment. Further, the confocal system incorporates a number of optical parts, including the dichroic mirror 118, and has a relatively complex structure.

Therefore, a need exists for a method and apparatus for detecting optically active molecules, such as charged bands of DNA fragments, in which alignment is simple and efficient and the structure is less complex and smaller than confocal systems. The present invention provides such a method and apparatus.

SUMMARY OF THE INVENTION

In accordance with the present invention, a method and apparatus is provided for illuminating an optically active sample and for collecting light emitted by the sample, using a fiber optic bundle and an optical apparatus (such as a lens set) for laser illumination and fluorescence collection.

In one embodiment, the present invention is a system for illuminating a fluorescently labeled sample and collecting light from the sample. The system comprises a fiber optic bundle, including at least one illuminating fiber for emitting an illuminating beam, and including a plurality of collecting fibers disposed around the illuminating fiber. The system further comprises an optical apparatus for focusing the illuminating beam, for directing the focused illuminating beam to the fluorescently labeled sample to cause the sample to emit fluoresced light, and for directing at least some of the fluoresced light to the collecting fibers.

In another embodiment, the present invention is a lens set for collecting and focusing light in a system having a fiber optic bundle and a fluorescently labeled sample supported by a sample carrier. The fiber optic bundle includes an illuminating fiber for emitting an illuminating beam and a plurality of collecting fibers disposed about the perimeter of the illuminating fiber for collecting fluoresced light emanating from the sample. The lens set includes a first lens, configured to shape the illuminating beam emitted by the illuminating fiber into a substantially columnar illuminating"

beam. The lens set also includes a second lens, configured to: (1) focus the columnar illuminating beam into a beam spot that strikes the sample, thereby causing the sample to emit fluoresced light; (2) shape at least some the fluoresced light into a substantially columnar fluoresced beam; and (3) direct the columnar fluoresced beam to the first lens. In the lens set, the first lens is further configured to focus a substantial portion of the fluoresced beam onto the collecting fibers.

In yet another embodiment, the present invention is a method for illuminating a fluorescently labeled sample and detecting fluoresced light emitted by the sample. The method includes the following steps: (a) emitting an illuminating beam from an illuminating fiber disposed in a fiber optic bundle; (b) focusing the illuminating beam by an optical apparatus and directing the focused illuminating beam to the fluorescently labeled sample, thereby causing the sample to emit fluoresced light; (c) collecting at least some of the fluoresced light by the optical apparatus and focusing the collected fluoresced light onto a plurality of collecting fibers disposed around the perimeter of the illuminating fiber in the fiber optic bundle; (d) collecting the focused fluoresced light by the collecting fibers; and (e) detecting the fluoresced light collected by the collecting fibers.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Throughout the remainder of this description, for convenience, reference will be made to DNA sequencing procedures, in which a sample containing fluorescently labeled nucleic acids (or DNA fragments) is illuminated, and the fluoresced light emitted by the DNA fragments is collected and detected. It will be recognized, however, that the present invention is not limited to DNA sequencing. Rather, the present invention can be used for illuminating and detecting any kind of scattered light, including Raman scattering, Raleigh scattering, and Mie scattering, as well as light emitted by any type of fluorescently labeled or optically active particles.

Moreover, it will be recognized that the present invention is not limited to scanning systems, in which the illuminating light is scanned across the sample. Rather, the present invention is intended to encompass scanning systems as well as stationary systems, in which the illuminating light is not scanned across the sample. Such a stationary orientation could be used, for example, to detect fluorescent light in a capillary electrophoresis system.

Figure 2:
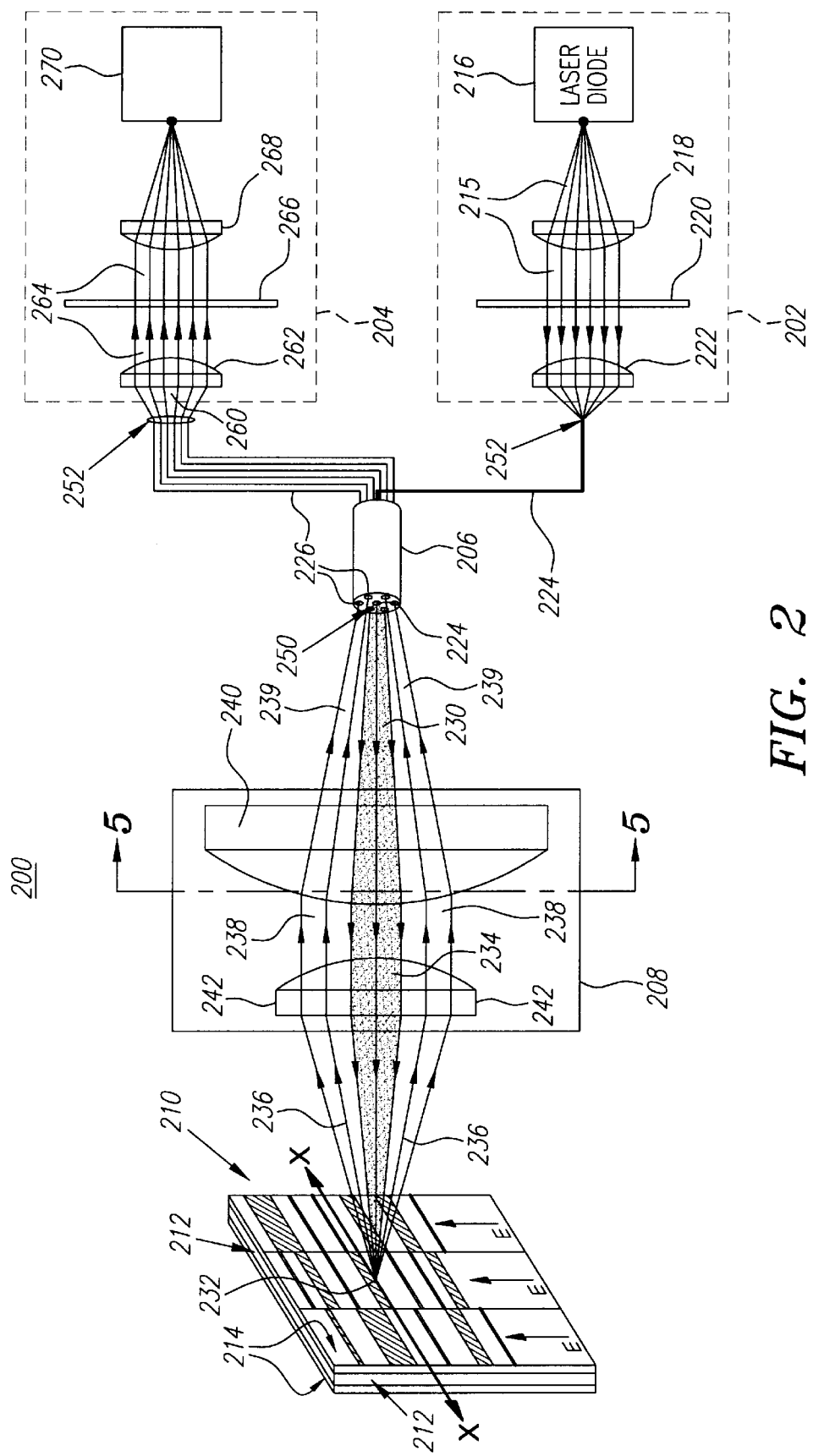
FIG. 2 shows an exemplary embodiment of a system in accordance with the present invention for illuminating a fluorescently labeled sample and for detecting fluoresced emissions from the sample.

FIG. 2 shows an exemplary embodiment of the system 200 of the present invention. The system 200 includes a light emitting assembly 202, a detecting assembly 204, a fiber optic bundle 206, a lens set 208, and a sample container 210. The fiber optic bundle includes an illuminating fiber 224 and a plurality of collecting fibers 226 disposed around the perimeter of the illuminating fiber 224. The sample container 210 supports a gel material 212, which contains a fluorescently labeled sample of DNA fragments. The gel 212 is supported between two substantially planar objects 214 (e.g., glass plates). The lens set 208 scans across the sample container 210 in the x-direction, as shown in FIG. 2.

The fiber optic bundle 206 preferably includes a plurality of individual collecting fibers 226, in the center of which is the illuminating fiber 224. In this configuration, the illuminating fiber 224 is placed on the geometric center of the lens set 208, with the collecting fibers 226 located off the geometric center of the lens set 208. This arrangement of the fiber optic bundle 206 is merely exemplary, however, and it will be recognized that the configuration of the fiber optic bundle 206 is dependent on the symmetry of the lens set 208. In the illustrated, preferred configuration, the lens set 208 consists of spherical lenses and thus has cylindrical symmetry. The fiber optic bundle 206 is therefore cylindrically arranged, as shown. Alternatively, for example, the lens set 208 could have cylindrical lenses and would thus have planar symmetry. In this case, the fiber optic bundle 206 would be arranged linearly.

Preferably, the lens set 208 includes spherical lenses (as will be described in detail below), and only a single illuminating fiber 224 is used, with five or more collecting fibers 226 bundled around the illuminating fiber 224 in a cylindrical configuration. It will be recognized, however, that the fiber optic bundle 208 may include more than one illuminating fiber and any number of collecting fibers. Two exemplary configurations of a suitable cylindrical fiber optic bundle are shown in FIGS. 3 and 4, which are described in detail below.

Figure 3:
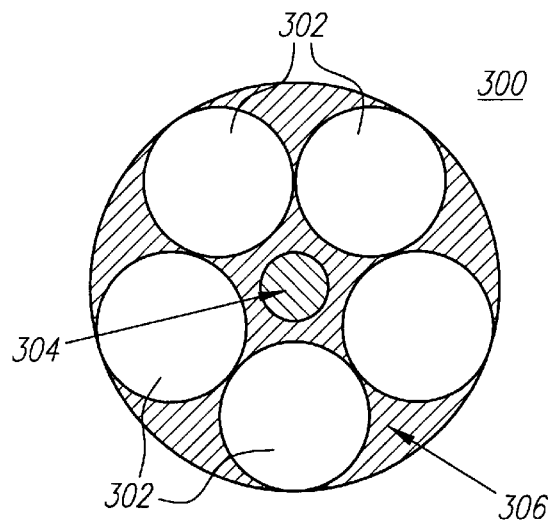
FIG. 3 is a cross-sectional view of an exemplary fiber optic bundle employed in the system of FIG. 2.
Figure 4:
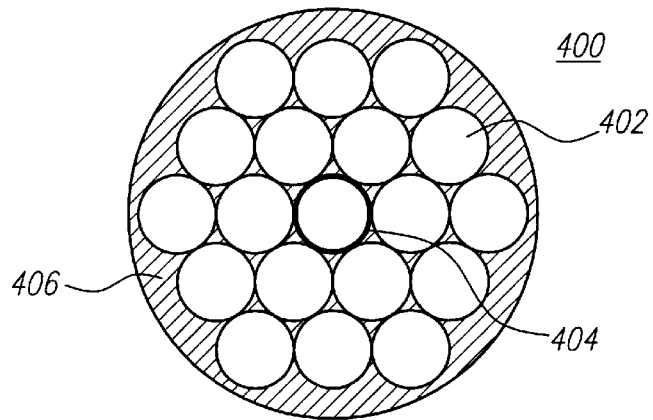
FIG. 4 is a cross-sectional view of an alternative embodiment of the fiber optic bundle employed in the system of FIG. 2.

FIG. 3 is a cross-sectional view of the preferred fiber optic bundle 300, which includes five collecting fibers 302 surrounding the perimeter of a single illuminating fiber 304. The illuminating fiber 304 has a diameter of about 90–120 microns, and is preferably about 100 microns. Further, the illuminating fiber 304 has a numerical aperture of about 0.12 or less, with the preferred numerical aperture being about 0.10. The relatively small numerical aperture of the illuminating fiber 304 restricts the cone of an illuminating light beam 230 output by fiber 304 to a fairly small angle, as can be seen in FIG. 2. The cone angle of the illuminating light beam 230 is determined by the following equation:

$$\text{Numerical Aperture} = \text{Sin } \theta/2, \qquad \text{Equation 1}$$

where $\theta$ is the angle of the cone of emitted light. For example, it can be seen from Equation 1 that a numerical aperture of 0.1 provides a cone angle of 11.5°. The size of the cone is maintained at a relatively small angle so that only the area of the lens set 208 with minimal aberration is used to process the illuminating light beam 230. It is preferred that the cone angle be about 12° or less.

Because the optics of the lens set 208 is preferably about 2×, the lens set 208 "demagnifies" or reduces the illuminating light beam 230 by ½ to create a spot 232 of about 50 microns in diameter that strikes the sample container 210. The five collecting fibers 302 have a diameter in a range of about 180–250 microns, with the preferred diameter being about 230 microns, and a numerical aperture of about 0.3 or greater. The configuration of five collecting fibers 302, rather than fewer collecting fibers, reduces the dead space around the illuminating fiber 304. Preferably, a nonfluorescing black material 306, such as epoxy, is used to fill the dead space around and between the bundled optical fibers 302, 304.

An alternative embodiment of the fiber optic bundle 400 is shown in the cross-sectional view of FIG. 4. This fiber optic bundle 400 also has a single illuminating fiber 404, but has eighteen collecting fibers 402 surrounding the illumination fiber 404. The illuminating fiber 404 has a diameter in a range of about 130–170 microns, with the preferred diameter being about 150 microns, and has a numerical aperture of about 0.12 or less, with the preferred numerical aperture being about 0.10. Again, the small numerical aperture of the illuminating fiber 404 restricts the output cone of the illuminating beam 230 to a fairly small angle, as described above. In this embodiment, the 2× optics of the lens set 208 reduces the illuminating beam 230 to a spot 232 of about 75 microns in diameter. The collecting fibers 402 have a diameter in a range of about 180–220 microns, with the preferred diameter being about 200 microns, and have a numerical aperture of about 0.3 or greater. Here, again, a nonfluorescing black epoxy 406 is preferably used to fill the spaces around and between the bundled optical fibers 402, 404.

The lens set 208 focuses the illuminating beam 230 to form the illuminating spot 232 (shown with shading), which strikes the sample carrier 210. In the preferred embodiment of FIG. 2, the lens set 208 includes a spherical lens 240 and an aspherical lens 242. The spherical lens 240 is located in front of the fiber optic bundle 206 and, in the preferred embodiment, is an 18 mm focal length spherical-plano lens (e.g., a Newport Corporation KPX040). The spherical lens 240, together with the small numerical aperture of the illuminating fiber 224, forms a substantially collimated illuminating beam 234 with minimal aberrations. The aspherical lens 242—preferably an 8 mm focal length, diffraction limited aspherical lens (such as a GelTech 350240)—is used to focus the collimated illuminating beam 234 to form the illuminating spot 232.

The illuminating spot 232 strikes the sample carrier 210, which supports the gel 212, which, in turn, contains the sample and its DNA fragments. A motive device (not shown) may be used to move the lens set 208, such that the illuminating spot 232 is scanned across the sample carrier 210. The fluorescently labeled DNA fragments that are illuminated by the spot 232 fluoresce light in an omnidirectional fashion. A portion 236 of the fluorescing light is then collected by the lens set 208. In particular, the aspherical lens 242, with a preferred numerical aperture of about 0.5 or greater, forms the collected fluorescing light 236 into a substantially collimated fluorescing beam 238. The spherical lens 240, preferably having a diameter matching that of the aspherical lens 242, then forms the collimated fluorescing beam 238 into a narrowing conical fluorescing beam 239 that is focused onto the collecting fibers 226.

Figure 5:
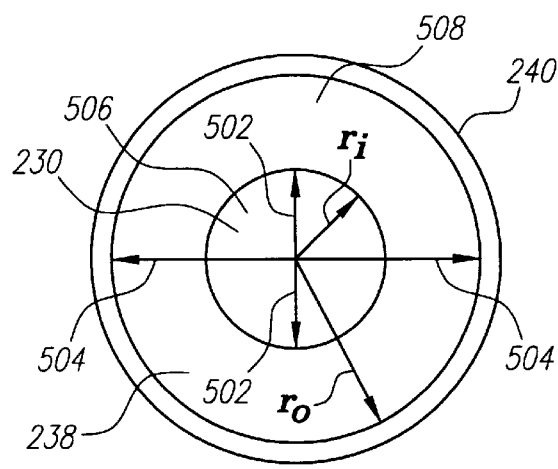
FIG. 5 is a cross-sectional view taken along line 5—5 of FIG. 2, showing the cross-sectional areas of an illuminating beam and fluoresced light emitted by a sample at a lens located adjacent a fiber optic bundle.

To obtain a good focus of the illuminating spot 232 in the gel 212, the illuminator fiber 224 directs the illuminating beam 230 toward an area on the spherical lens 240 where spherical aberration is minimal. When the illuminating beam 230 strikes the spherical lens 240, the beam 230 has an inner diameter 502, as shown in FIG. 5, which is a cross-sectional view taken along line 5—5 of FIG. 2. In the exemplary embodiment described herein, the inner diameter 502 is in a range of about 3.5 to 4.5 mm, preferably about 4 mm. Thus, the collimated illuminating beam 234 will also have a diameter of about 4 mm. The fluorescent light beam 236 collected by the lens set 208 strikes the aspherical lens 242, which forms the beam 236 into the collimated fluorescing beam 238, which has an outer diameter 504 when it strikes the spherical lens 240, as is also shown in FIG. 5. In the exemplary embodiment herein, the outer diameter 504 is in a range of about 7.5 to 9 mm, preferably about 8 mm. The balance between the inner diameter 502 and the outer diameter 504 determines the optical coupling between the fiber bundle 206 and the gel 212.

In accordance with the present invention, the majority of the rays outside of the inner diameter 502 of the spherical lens 240 are aberrated onto the collecting fibers 226, rather than being focused onto the illuminating fiber 224. FIG. 5 shows that the illuminating beam 230 has a substantially circular cross-sectional area 506, with a radius $r_i$, at the spherical lens 240. FIG. 5 also shows that the collimated fluoresced beam 238 has a substantially circular cross-sectional area, with a radius $r_o$, larger than $r_i$ of the illuminating beam 230, forming an annular area 508 encircling the cross-sectional area 506 of the illuminating beam 230. The ratio of the cross-sectional area 506 to the annular area 508 determines the collection efficiency (CE) into the inner, illuminating fiber 224. The collection efficiency of the outer, collecting fibers 226 is determined by the following equation:

$$CE = 1 - \pi r_i^2 / \pi r_o^2. \qquad \text{Equation 2}$$

Taking Equation 2, and assuming that $r_i$ is 4 mm and $r_o$ is 8.68 mm, the collection efficiency (CE) of the collecting fibers 226 is 0.78 (i.e., CE=1−π(4)²/π(8.68)²=0.78).

Other loss terms in the fiber optic bundle 206, besides losses due to imperfect collection efficiency, include packing fraction and Fresnel losses on the uncoated fibers themselves. Packing fraction is caused by the dead space between the fibers 224, 226 when they are arranged into a bundle, as seen in FIGS. 3 and 4. For example, for the five 230 micron collecting fibers 302 of FIG. 3, the packing fraction (PF) is approximately 0.78 in the active area of the bundle; that is approximately 78% of the light is collected, and the remainder impinges on inactive areas of the bundle. This number would improve in a multiple row configuration. The Fresnel losses ($F_l$) on the interface surfaces 250, 252 of the fiber optic bundle 206 is typically 4% for each surface. The total transmission ($T_t$) of the fiber bundle system is the product of the following:

$$T_t = (CE)(PF)(1 - F_{l\text{-}surface\ 250})(1 - F_{l\text{-}surface\ 252}) \qquad \text{Equation 3}$$

Thus, for the exemplary embodiment described above, the total transmission is 0.56 or 56% (i.e., $T_t$=(0.78)(0.78)(1−0.04)(1−0.04)=0.56).

Figure 1:
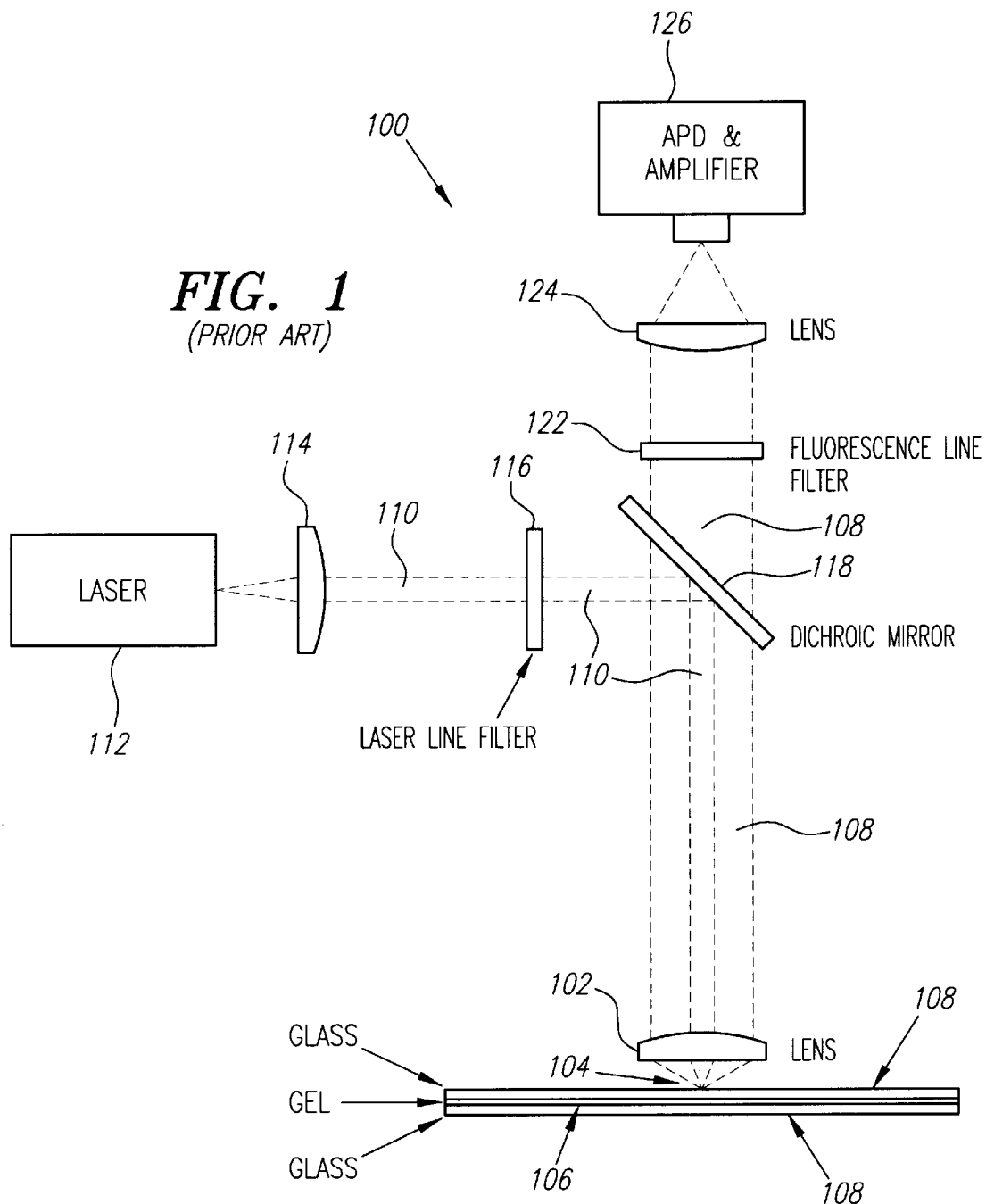
FIG. 1 shows a prior art confocal scanning system for scanning a sample and for detecting fluoresced light, in which the same lens is used to focus the illuminating beam onto a fluorescently labeled sample and to collect the fluoresced light emitted by the sample.

The lost 44% of light results from the use of optical fibers 224, 226 instead of the confocal lens systems of the prior art, such as that shown in FIG. 1. The signal-to-noise ratio of the present invention, however, provides a significant advantage over confocal systems, offsetting, at least to some extent, the light signal losses. In the prior art confocal systems, the predominate noise source is the laser light reflected back into the dichroic mirror 118. In the present invention, with the illuminating fiber 224 in the center of the fiber optic bundle 206, the back-reflected light is directed into the illuminating fiber 224 and not into the detection leg 204 of the system 200. This may result in a significant noise reduction in the present system may compensate for the losses in overall light signal.

The light emitting assembly 202 launches an input light beam 215 into the illuminating fiber 224. The light emitting assembly 202 includes a light source 216, which may be a laser diode (e.g, a Sharp LT024MD 30 mW laser diode). The light source 216 emits the input light beam 215, which is collimated by the first aspheric lens 218, which preferably has a focal length of 3.1 mm. A commercially available example of the first aspheric lens 218 is the Thorlabs C330TM-B. The collimated input beam 215 passes through a narrow band interference filter 220, which blocks wavelengths in the collimated input beam 215 that are in the wavelength of fluoresced light. A second aspheric lens 222, with a preferred focal length of 15.36 mm (such as the Thorlabs C260TM-B), is used to focus the filtered, collimated input beam 215 onto the face 252 of the illuminating fiber 224. The long focal length of the second aspheric lens 222, combined with the small diameter of the input light beam 215, allows the light beam 215 to be launched into an illuminating fiber 224 with a relatively small numerical aperture (e.g., 0.12 or less).

The detection assembly 204 detects output light 260, which is emitted by the collecting fibers 226 at a relatively large numerical aperture. The detection assembly 204 includes a first large aspherical lens 262 to collect output light 260. In the preferred embodiment, the first aspherical lens 262 has an 18 mm focal length and a 24 mm diameter (such as the Melles Griot 01 LAG 005). The first aspherical lens 262 forms a collimated beam of output light 264 that passes through an interference filter 266. Preferably, the interference filter 266 passes only about a 25 nm wide band in the center of the fluoresced light spectra. In the spectra of the laser, the interference filter 266 is designed to attenuate heavily. A second large aspherical lens 268, similar to (or the same as) the first lens 262, is used to focus the filtered, collimated beam 264 onto a light detector 270. The preferred detector is a large area avalanche photodiode detector, such as the Hamamatsu C5460-01 3 mm avalanche photodiode detector module.

In the present invention, alignment of the system 200 is accomplished in a modular fashion, providing a significant advantage over confocal systems, such as the one shown in FIG. 1. In the system 100 of FIG. 1, alignment of each part of the system 100 is interdependent, meaning that adjustment to any one part of the system requires adjustment of all other parts. The system 200 of the present invention breaks the alignment process into three separate, mechanically unrelated modules: (1) light emitting assembly 202, including laser 216, collimating lens 218, filter 220, and coupling lens 222; (2) the lens set 208, including the collimating lens 240 and aspherical object lens 242; and (3) detector assembly 204, including collimating lens, filter 266, coupling lens 268, and detector 270. These modules can be aligned independently, meaning that an adjustment to any one of the modules does not require an adjustment to any other in order to properly align the system 200.

The present system 200 also increases the design flexibility, because any one of the three modules may be independently positioned without impact to any of the others. Because the fiber optic bundle 206 is flexible, it may be arbitrarily routed, and module 1 (assembly 202) and module 3 (assembly 204) may be positioned anywhere with respect to the scanning lens set 208 (i.e., module 2). The lens set 208, of course, should be positioned in close proximity to the gel 212.

A number of embodiments of the present invention have been described. Nevertheless, it will be understood that various modifications may be made without departing from the spirit and scope of the invention. For example, the present invention has been described with specific reference to DNA sequencing. It will be recognized, however, as noted above, that the present invention is not limited to DNA sequencing and can be used in any application in which fluorescently labeled particles are being scanned. Further, the preceding description has, in some instances, referred to specific embodiments of the various elements of the system 200, such as the lenses and optical fibers. It will be further recognized that those embodiments are merely exemplary and that suitable alternative embodiments exist. Accordingly, it is to be understood that the invention is not to be limited by the specific illustrated embodiment, but only by the scope of the appended claims.

What is claimed is:

1. A system for illuminating a fluorescently labeled sample and for collecting fluoresced light emitted by the sample, the system comprising:

(a) a fiber optic bundle, including at least one illuminating fiber for emitting an illuminating beam, and including at least one collecting fiber disposed adjacent the illuminating fiber; and (b) an optical apparatus for focusing the illuminating beam, for directing the focused illuminating beam to the fluorescently labeled sample to cause the sample to fluoresce, and for directing at least some of the fluorescence from the sample through an aberrating area of the optical apparatus configured to cause aberration of the fluorescence and direct a substantial portion of the fluorescence onto the collecting fibers, and wherein the optical apparatus comprises at least one spherical lens and an optical axis, the illuminating fiber being positioned substantially along the optical axis and the collecting fibers being located off the optical axis in the aberrating area of the optical apparatus where the optical axis aberrates light rays.

2. The system of claim 1 wherein the optical apparatus includes:

(a) the at least one spherical lens for collimating the illuminating beam; and (b) an aspherical lens for focusing the collimated illuminating beam into a spot that strikes the sample and for collimating at least some the fluorescence and directing the collimated fluorescence to the spherical lens;

wherein the spherical lens is further for focusing the collimated fluorescence onto the collecting fibers.

3. The system of claim 2 wherein the illuminating beam is directed to an illuminating area characterized by minimal aberration on the spherical lens; and wherein a majority of the collimated fluorescence striking the spherical lens outside the illuminating area passes through the aberrating area onto the collecting fibers.

4. The system of claim 3 wherein the illuminating area has an illuminating radius ($r_i$) and the collimated fluorescence striking the spherical lens outside the illuminating area forms an annular area having an outside annular radius ($r_o$);

and wherein the collection fibers have a collection efficiency (CE), such that $CE = 1-(\pi r_i^2 / \pi r_o^2)$.

5. The system of claim 3 wherein the aspherical lens has a numerical aperture greater than or equal to about 0.2.

6. The system of claim 2 wherein the aspherical lens has an aspherical focal length ($FL_a$) and the spherical lens has a spherical focal length ($FL_s$); and wherein $FL_a/FL_s$ is in the range of about 2 to about 2.5.

7. The system of claim 6 wherein the $FL_a$ is approximately 18 mm and $FL_s$ is approximately 8 mm.

8. The system of claim 1 wherein the illuminating fiber has a diameter; and wherein the optical apparatus reduces the illuminating beam, such that the diameter of the illuminating beam striking the sample is less than or equal to about ½ of the diameter of the illuminating fiber.

9. The system of claim 8 wherein the illuminating fiber has a numerical aperture of less than or equal to about 0.12, and each collecting fiber has a numerical aperture of greater than or equal to about 0.3.

10. The system of claim 1 wherein the illuminating fiber is surrounded by at least five collecting fibers, and each collecting fiber has a greater numerical aperture than the illuminating fiber.

11. The system of claim 1 wherein the sample includes fluorescently labeled DNA fragments and the sample carrier is a gel formed into a planar configuration.

12. The system of claim 11 wherein the fluorescently labeled sample is supported by a gel disposed between two substantially planar objects, and an electric field is applied to the gel at an end of the planar objects causing the DNA fragments to propagate through the gel away from the end of the planar objects to which the electric field is applied.

13. The system of claim 12 wherein a plurality of lanes are formed between the planar objects extending from one end to another end of the planar objects, and the electric field is applied such that the sample propagates through the lanes.

14. The system of claim 1 wherein the fiber optic bundle is in a cylindrical configuration and a plurality of collecting fibers surround the illuminating fiber.

15. The system of claim 1 wherein the illuminating beam is scanned across the sample.

16. A lens set for collecting and focusing light in a system having a fiber optic bundle and a fluorescently labeled sample supported by a sample carrier, the fiber optic bundle including an illuminating fiber for emitting an illuminating beam and a plurality of collecting fibers disposed about the perimeter of the illuminating fiber for collecting fluorescence from the sample, the lens set comprising:

(a) a first lens, configured to shape the illuminating beam emitted by the illuminating fiber into a substantially columnar illuminating beam;

(b) a second lens, configured to:
  (1) focus the columnar illuminating beam into a beam spot that strikes the sample, thereby causing the sample to fluoresce,
  (2) shape at least some of the fluorescence into a substantially columnar fluoresced beam, and
  (3) direct the columnar fluoresced beam to the first lens; and (c) the first lens being further configured to cause aberration which directs a substantial portion of the fluoresced beam onto the collecting fibers.

17. The lens set of claim 16 wherein the first lens includes a spherical lens; wherein the illuminating beam is directed to an illuminating area on the spherical lens; and wherein a majority of the fluoresced beam striking the spherical lens outside the illuminating area is aberrated onto the collecting fibers.

18. The lens set of claim 17 wherein the second lens includes an aspherical lens having an aspherical focal length ($FL_a$); wherein the spherical lens has a spherical focal length ($FL_s$); and wherein $FL_a/FL_s$ is in the range of about 2 to about 2.5.

19. The lens set of claim 18 wherein the $FL_a$ is approximately 18 mm and the $FL_s$ is approximately 8 mm.

20. The lens set of claim 16 wherein the second lens includes an aspherical lens having a numerical aperture greater than or equal to about 0.2.

21. The lens set of claim 16 wherein the illuminating beam is passed through an area of the first lens characterized by minimal aberration.

22. A method for illuminating a fluorescently labeled sample and detecting fluoresced light emitted by the sample comprising:

(a) emitting an illuminating beam from an illuminating fiber disposed in a fiber optic bundle;

(b) focusing the illuminating beam by an optical apparatus, by shaping the illuminating beam into a substantially columnar shape by a first lens, directing the substantially columnar illuminating beam to a second lens, and focusing the substantially columnar illuminating beam by the second lens into a beam spot that strikes the sample, thereby causing the sample to fluoresce;

(c) collecting at least some of the fluorescence by the second lens, shaping the collected fluorescence into a substantially columnar beam having a diameter greater than the diameter of the substantially columnar illuminating beam, directing the substantially columnar fluoresced beam to the first lens and directing the collected fluorescence through an area of the first lens configured to cause aberration of the fluorescence and direct the fluorescence onto at least one collecting fiber disposed adjacent the perimeter of the illuminating fiber in the fiber optic bundle;

(d) collecting the focused fluorescence by the collecting fiber; and (e) detecting the fluorescence collected by the collecting fiber.

23. The method of claim 22, further comprising scanning the illuminating beam across the sample.

* * * * *